United States Patent
Evitt et al.

(10) Patent No.: US 8,039,679 B2
(45) Date of Patent: Oct. 18, 2011

(54) BISPHENOL-A PLANT YIELD ENHANCEMENT

(75) Inventors: Steven D. Evitt, Somerville, MA (US); Stephen W. Fetsko, Hingham, MA (US); Chung-Ming Chi, Needham, MA (US)

(73) Assignee: Badger Licensing LLC, Cambridge, MA (US)

( * ) Notice: Subject to any disclaimer, the term of this patent is extended or adjusted under 35 U.S.C. 154(b) by 448 days.

(21) Appl. No.: 12/066,630

(22) PCT Filed: Aug. 24, 2006

(86) PCT No.: PCT/US2006/033084
§ 371 (c)(1),
(2), (4) Date: Aug. 18, 2008

(87) PCT Pub. No.: WO2007/044139
PCT Pub. Date: Apr. 19, 2007

(65) Prior Publication Data
US 2009/0221858 A1  Sep. 3, 2009

Related U.S. Application Data

(60) Provisional application No. 60/724,415, filed on Oct. 7, 2005.

(51) Int. Cl.
*C07C 37/74* (2006.01)
*C07C 37/20* (2006.01)

(52) U.S. Cl. ............... 568/723; 568/724; 568/728

(58) Field of Classification Search .............. None
See application file for complete search history.

(56) References Cited

U.S. PATENT DOCUMENTS

| | | | |
|---|---|---|---|
| 3,936,507 A * | 2/1976 | Ligorati et al. | 568/724 |
| 4,188,496 A | 2/1980 | Jaquiss et al. | |
| 4,277,628 A | 7/1981 | Carnahan | |
| 4,327,229 A | 4/1982 | Mendiratta | |
| 4,351,966 A | 9/1982 | Flock | |
| 4,490,566 A * | 12/1984 | Chang et al. | 568/798 |
| 4,717,777 A | 1/1988 | Garces et al. | |
| 4,927,978 A * | 5/1990 | Buechele et al. | 568/724 |
| 4,950,805 A | 8/1990 | Iimuro et al. | |
| 5,345,000 A | 9/1994 | Moriya et al. | |
| 5,504,251 A | 4/1996 | Dyckman et al. | |
| 5,672,774 A | 9/1997 | Dyckman et al. | |
| 5,777,180 A * | 7/1998 | June et al. | 568/728 |
| 6,133,486 A | 10/2000 | Maas et al. | |
| 6,191,316 B1 | 2/2001 | Fennhoff et al. | |
| 6,294,702 B1 | 9/2001 | Fennhoff et al. | |
| 6,303,835 B1 | 10/2001 | Shafer et al. | |
| 6,307,111 B1 | 10/2001 | Fennhoff et al. | |
| 6,459,004 B1 | 10/2002 | Ono et al. | |
| 6,806,394 B2 | 10/2004 | Evitt et al. | |

FOREIGN PATENT DOCUMENTS

| | | |
|---|---|---|
| CN | 1041581 A | 4/1990 |
| CN | 1255112 A | 5/2000 |
| CN | 1300273 A | 6/2001 |
| EP | 0 439 632 A1 * | 8/1991 |
| EP | 1 120 753 | 3/2005 |
| GB | 905994 | 9/1962 |

OTHER PUBLICATIONS

Office Action issued on Aug. 26, 2010 in the corresponding Chinese Application No. 200680037195.0.

* cited by examiner

*Primary Examiner* — Rosalynd Keys
(74) *Attorney, Agent, or Firm* — Roberts Mlotkowski Safran & Cole, P.C.

(57) ABSTRACT

An improved process is provided for producing bisphenol-A (BPA) comprising steps of (1) contacting benzene and a $C_3$ alkylating agent to produce an alkylation effluent comprising cumene; (2) oxidizing the cumene to produce the corresponding hydroperoxide; (3) cleaving the hydroperoxide to produce product comprising phenol and acetone; (4) reacting acetone with phenol to form a reaction product stream comprising crude bisphenol-A product; (5) distilling the reaction product stream, while sending downstream to a BPA-phenol adduct crystallization and purification step, the resulting concentrated BPA phenolic feed stream; (6) producing BPA-phenol adduct crystals by crystallization of the concentrated BPA phenolic feed stream; (7) separating the BPA-phenol adduct crystals by solid-liquid separationr; (8) cracking a stream comprising at least a portion of said final mother liquor to recover a product; and (9) recovering and feeding the phenol product of step (8) to step (4) and/or step (7).

14 Claims, No Drawings

BISPHENOL-A PLANT YIELD ENHANCEMENT

CROSS REFERENCE TO RELATED APPLICATIONS

This application is a 35 U.S.C. 371 National Stage Application of International Application No. PCT/US2006/033084, filed Aug. 24, 2006, which claims the benefit of Provisional Application No. 60/724,415, filed Oct. 7, 2005, the disclosures of which are hereby incorporated by reference in their entireties.

FIELD OF THE INVENTION

The present invention relates to an improvement in the yield of an integrated process for producing bisphenol-A (BPA). BPA is a commercially significant compound used to manufacture polycarbonates, other engineering thermoplastics and epoxy resins. The polycarbonate application in particular demands high purity BPA due to stringent requirements for optical clarity and color in the finished application. Accordingly, those skilled in the art continually strive to improve the product quality of bisphenol-A in economically efficient process schemes. The present invention concerns a new process scheme to produce high purity BPA in improved yield.

BACKGROUND OF THE INVENTION

BPA and its manufacture in the prior art is described U.S. Pat. No. 4,950,805 (Iimuro, et al.), U.S. Pat. No. 5,345,000 (Moriya et al.) and U.S. Pat. No. 6,806,394 (Evitt, et al.), which patents are incorporated herein by reference.

BPA is produced commercially by the condensation of acetone and phenol over an acid catalyst and, in fact, BPA production is the largest consumer of phenol. Currently, the most common route for the production of phenol comprises a three-step process in which the first step involves alkylation of benzene with propylene to produce cumene, followed by oxidation of the cumene to the corresponding hydroperoxide, and then cleavage of the hydroperoxide to produce equimolar amounts of phenol and acetone.

The production of BPA consumes two moles of phenol and one mole of acetone for each mole of BPA produced. According to the present invention, an integrated process in which part of the required phenol is produced from cumene, and part is produced by a heavies cracking stage, yield of the overall process is improved economically.

In the manufacture of BPA by current procedures, residue comprising some phenol, BPA and BPA byproduct is lost, usually being used as a fuel component. In the present integrated process, typical BPA byproduct residue losses are converted to phenol that is recycled and used in the reaction with acetone to reduce the overall consumption of phenol in the production of BPA.

SUMMARY OF THE INVENTION

In one aspect, the present invention resides in an improved process for producing BPA comprising:
(1) contacting benzene and a $C_3$ alkylating agent, e.g. propylene, isopropanol or propyl chloride, under alkylation conditions with an alkylation catalyst in a reaction zone to produce an alkylation effluent comprising cumene;
(2) oxidizing the cumene from step (1) to produce the corresponding hydroperoxide;
(3) cleaving the hydroperoxide from step (2), to produce product comprising phenol and acetone;
(4) reacting acetone with a stoichiometric excess of phenol under acidic conditions, possibly in the presence of a cocatalyst or promoter, e.g. a thiol compound, to form a reaction product stream comprising crude bisphenol-A product, unreacted phenol, possibly unreacted acetone, possibly cocatalyst or promoter, water of condensation, and other reaction byproducts;
(5) distilling in single or multistage the reaction product stream from step (4) to distill off a volatilized unreacted phenol stream, possibly an unreacted acetone stream, possibly a stream containing cocatalyst or promoter if present in step (4), and the water of condensation, while sending downstream to a BPA-phenol adduct crystallization and purification step, said purification step comprising one or more solid-liquid separation and wash steps, the resulting concentrated BPA phenolic feed stream consisting essentially of phenol in which the bisphenol-A and byproducts have been concentrated;
(6) producing BPA-phenol adduct crystals by crystallization of the concentrated BPA phenolic feed stream in said crystallization, solid-liquid separation and wash steps with cooling for said crystallization by vaporization of an alkane hydrocarbon or mixture of hydrocarbons containing from 4 to 6 carbons, e.g. pentane;
(7) separating the BPA-phenol adduct crystals by solid-liquid separation, such as, for example, by centrifugation or filtration, and washing same in one or multiple stages with a wash phenol stream which may include at least a portion of the volatilized unreacted phenol stream recovered from step (5), or spent wash or mother liquor from subsequent crystallization, solid-liquid separation, and wash steps, to produce final washed BPA-phenol adduct, final spent wash and final mother liquor;
(8) cracking a stream comprising at least a portion, for example from about 0.5 to about 20 wt. %, preferably from about 1 to about 10 wt. %, more preferably from about 2 to about 7 wt. %, of said final mother liquor of step (7) in a reactor with basic or acidic cracking catalyst, for example caustic or aluminum chloride, under cracking conditions selected to recover a product comprising from about 60 to about 90 wt. % of said portion of said final mother liquor stream as phenol having a purity level of from about 95 to about 100 wt. %, and from about 10 to about 40 wt. % of said cracked stream as heavy residue byproduct; and
(9) recovering and feeding the phenol product of step (8) to step (4) and/or step (7).

It is important to note that cracking step (8) may precede a distillation, follow a distillation or be within a distillation system, e.g. in the distillation bottoms, so long as the cracking conditions are specifically selected as herein detailed to provide the required results. Further, the heavy residue byproduct of step (8) comprises less than about 40 wt. %, preferably from about 0.01 to about 30 wt. %, more preferably from about 1 to about 12 wt. % phenol to allow for ease of processing. Non-limiting examples of acidic cracking catalysts for use in step (8) include hydrochloric acid, sulfuric acid, aluminum chloride, zirconium chloride and zirconium sulfate.

Conveniently, the $C_3$ alkylating agent in step (1) comprises propylene or isopropanol.

The alkylation catalyst in step (1) above may comprise a molecular sieve selected from the group consisting of zeolite Beta, faujasite, mordenite, MCM-22, PSH-3, SSZ-25, ERB-1, ITQ-1, ITQ-2, MCM-36, MCM-49, MCM-56 and mixtures thereof. Preferably, said molecular sieve is selected from the group consisting of MCM-22, PSH-3, SSZ-25, ERB-1, ITQ-1, ITQ-2, MCM-36, MCM-49, MCM-56 and mixtures thereof.

In one embodiment, said contacting step (1) is conducted under at least partial liquid phase conditions. Conveniently, said alkylation conditions include a temperature of up to about 250° C., a pressure up to about 250 atmospheres (25,000 kPa), a benzene to $C_3$ alkylating agent, e.g. propylene, ratio from about 1 to about 10 and a benzene weight hourly space velocity (WHSV) from about 5 $hr^{-1}$ to about 250 $hr^{-1}$.

In one embodiment, said alkylation effluent produced in step (1) comprises polyisopropylbenzenes and the process further comprises contacting said polyisopropylbenzenes with benzene in the presence of a transalkylation catalyst to produce cumene. Conveniently, the transalkylation catalyst comprises a molecular sieve selected from the group consisting of zeolite Beta, faujasite, mordenite, USY, MCM-22, MCM-68, PSH-3, SSZ-25, ERB-1, ITQ-1, ITQ-2, MCM-36, MCM-49, MCM-56 and mixtures thereof.

The oxidizing step (2) may or may not be conducted in the presence of a catalyst, which catalyst can be a homogeneous catalyst or more preferably is a heterogeneous catalyst. Conveniently, the oxidizing step (2) is conducted at a temperature of from about 60° C. to about 200° C. and a pressure of from about 0 to about 1000 kPa.

Conveniently, the cleaving step (3) is conducted in the presence of a catalyst, which can be a homogeneous catalyst or a heterogeneous catalyst. Cleaving step (3) is conducted at a temperature of from about 20° C. to about 150° C., such as for example from about 40° C. to about 120° C., a pressure of from about 0 to about 7000 kPa, such as for example from about 100 to about 2860 kPa, and a liquid hourly space velocity (LHSV) based on the hydroperoxide of from about 0.1 to about 100 $hr^{-1}$, preferably from about 1 to about 50 $hr^{-1}$.

Suitable catalysts for step (4) include inorganic and organic acids, such as sulfuric acid and hydrogen chloride, and cationic exchange resins, optionally together with a cocatalyst or promoter, including a thiol promoter such as an alkyl mercaptan. As a non-limiting example, the condensation reaction of step (4) may be conducted in the presence of added promoter, non-limiting examples of which include methyl mercaptan, ethyl mercaptan, 2,2-bis(methylthio)propane, and mercaptocarboxylic acid, e.g. mercaptopropionic acid. As further non-limiting examples, the condensation reaction of step (4) may be conducted in the presence of added promoters comprising promoter-bound resins, including resins ionically-bound to quaternary amine groups contained in mercaptoalkylpyridines, or mercaptoalkylamines, the latter most often being 2-mercaptoethylamine derived from hydrolysis of 2,2 dimethylthiozolidine.

Conveniently, at least one of, and preferably each of, the contacting step (1), oxidizing step (2) and cleaving step (3) may be effected by catalytic distillation.

DETAILED DESCRIPTION OF THE EMBODIMENTS

The present invention is directed to an improved, economical integrated process for producing BPA. The process employs cumene as the source of the acetone and part of the phenol required to produce the BPA and employs a cracking stage to produce part of the phenol needed for production of the BPA.

Alkylating benzene with a C3 alkylating agent, such as propylene, produces cumene. The cumene is suitably purified by a fraction method. The purified cumene is then oxidized to cumene hydroperoxide, which is subsequently decomposed to phenol and acetone.

Fractionation of the cleavage products produces phenol and acetone product streams, which can then be reacted to produce the desired BPA.

Cumene Production

The benzene employed in the alkylation step to produce cumene can be any commercially available benzene feed, but preferably the benzene has a purity level of at least 99 wt. %.

The alkylating agent can be any aliphatic or aromatic organic compound having one or more available alkylating aliphatic groups capable of reaction with benzene and having 3 carbon atoms, or mixtures thereof. Examples of suitable $C_3$ alkylating agents include propylene; alcohols (inclusive of monoalcohols, dialcohols, trialcohols, etc.), such as n-propanol; aldehydes, such as propionaldehyde; and propyl halide, such as propyl chloride, or mixtures thereof with propylene being particularly preferred.

The alkylation catalyst used in the present process comprises a molecular sieve selected from the group consisting of zeolite Beta (described in U.S. Pat. No. 3,308,069), faujasite, mordenite, including dealuminized mordenite, members of the MCM-22 family of molecular sieves and mixtures thereof. Molecular sieves of the MCM-22 family include MCM-22 (described in U.S. Pat. No. 4,954,325), PSH-3 (described in U.S. Pat. No. 4,439,409), (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575) and MCM-56 (described in U.S. Pat. No. 5,362,697). Preferred catalysts are members of the MCM-22 family.

The alkylation catalyst can include the molecular sieve in unbound or self-bound form or, alternatively, the molecular sieve can be combined in a conventional manner with an oxide binder, for example alumina, such that the final alkylation catalyst contains between about 2 and about 80 wt. % molecular sieve.

The alkylation process is conducted such that the organic reactants, i.e., the benzene and $C_3$ alkylating agent, are brought into contact with the alkylation catalyst in a suitable reaction zone such as, for example, in a flow reactor containing a fixed bed of the catalyst composition or in a catalytic distillation reactor, under effective alkylation conditions. Such conditions include a temperature of up to about 250° C., e.g., up to about 150° C., e.g., from about 10° C. to about 125° C.; a pressure of about 250 atmospheres (25,000 kPa) or less, e.g., from about 1 to about 30 atmospheres (100 to 3,000 kPa); a benzene to alkylating agent, e.g. propylene, ratio from about 1 to about 10 and a benzene weight hourly space velocity (WHSV) from about 5 $hr^{-1}$ to about 250 $hr^{-1}$, preferably from about 5 $hr^{-1}$ to about 50 $hr^{-1}$.

The alkylation reactants can be in either the vapor phase or partially or completely in the liquid phase and can be neat, i.e. free from intentional admixture or dilution with other material, or they can be brought into contact with the alkylation catalyst composition with the aid of carrier gases or diluents such as, for example, hydrogen or nitrogen. Conveniently, the total feed to the alkylation step contains less than 1000 wppm (weight ppm, based on the weight of the feed), such as less than 500 wppm, for example less than 100 wppm, water. In addition, the total feed typically contains less than 100 wppm (weight ppm, based on the weight of the feed), such as less than 30 wppm, for example less than 3 wppm, sulfur and less than 10 wppm (weight ppm, based on the weight of the feed), such as less than 1 wppm, for example less than 0.1 wppm, nitrogen.

Although the alkylation step is highly selective towards cumene, the effluent from the alkylation reaction will normally contain some polyalkylated products, e.g. polyalkylbenzene, as well as unreacted aromatic feed and the desired monoalkylated species. The unreacted aromatic feed is normally recovered by distillation and recycled to the alkylation reactor. The bottoms from this distillation are further distilled to separate the cumene product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically effected in a transalkylation reactor, separate from the alkylation reactor, over a suitable transalkylation catalyst, such as an MCM-22 family catalyst, zeolite Omega, zeolite Beta, MCM-68 (see U.S. Pat. No. 6,014,018), zeolite Y, mordenite or a mixture thereof. The transalkylation reaction is typically conducted under at least partial liquid phase conditions. Suitable transalkylation conditions include a temperature of from about 50° C. to about 500° C., a pressure of from about 10 kPa to about 3,500 kPa, a weight hourly space velocity of from about 0.5 to about 500 hr$^{-1}$ on total feed, and benzene/polyalkylbenzene weight ratio of from about 0.1 to about 10.

Cumene Oxidation

The cumene product of the alkylation step described above is then oxidized to produce the corresponding hydroperoxide. The oxidation step is accomplished by introducing an oxygen-containing gas, such as air, into a liquid phase containing the cumene. The reaction can be performed in the absence of a catalyst, but the reaction rate can be improved by performing the oxidation in the presence of a catalyst, such as a water-soluble chelate compound in which multidentate ligands are coordinated to at least one metal selected from the group consisting of cobalt, nickel, manganese, copper, iron and mixtures thereof (See U.S. Pat. No. 4,013,725). A heterogeneous catalyst may be used. Suitable heterogeneous catalysts are described in U.S. Pat. No. 5,183,945, wherein the catalyst is an oxo (hydroxo) bridged tetranuclear manganese complex, and in U.S. Pat. No. 5,922,920, wherein the catalyst comprises an oxo (hydroxo) bridged tetranuclear metal complex having a mixed metal core, one metal of the core being a divalent metal selected from the group consisting of Zn, Cu, Fe, Co, Ni, Mn and mixtures thereof, and another metal being a trivalent metal selected from the group consisting of In, Fe, Mn, Ga, Al and mixtures thereof. The entire disclosures of said U.S. patents are incorporated herein by reference.

Other suitable catalysts for the oxidation step are the N-hydroxy substituted cyclic imides described in Published U.S. Patent Application No. 2003/0083527 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. These materials can be used either alone or in the presence of a free radical initiator and can be used as liquid phase, homogeneous catalysts or can be supported on a solid carrier to provide a heterogeneous catalyst.

Suitable conditions for cumene oxidation include a temperature from about 60° C. to about 200° C., such as from about 80° C. to about 120° C., and a pressure of from about 0 to about 1000 kPa.

A basic buffering agent may be added to the oxidation reaction to combine with acidic by-products that may form during the oxidation. In addition, an aqueous phase may be introduced, which can help dissolve basic compounds, such as sodium carbonate. The per-pass conversion in the oxidation step is preferably kept below about 50%, usually below about 30%, to minimize the formation of by-products. The hydroperoxides produced may be concentrated by distilling off the unreacted alkylbenzene prior to the cleavage step.

Hydroperoxide Cleavage

The cumene hydroperoxide produced in the oxidation step is subsequently cleaved to produce phenol and acetone. The cleavage reaction is conveniently carried out in the presence of a catalyst in the liquid phase at a temperature of from about 20° C. to about 150° C., such as from about 40° C. to about 120° C., a pressure of from about 0 to about 7000 kPa, such as from about 100 to about 2860 kPa, and a liquid hourly space velocity (LHSV) based on the hydroperoxide of from about 0.1 to about 100 hr$^{-1}$, preferably from about 1 to about 50 hr$^{-1}$. The hydroperoxide is preferably diluted in an organic solvent inert to the cleavage reaction, such as, for example, cumene, phenol or acetone, to assist in heat removal. The cleavage reaction is sometimes conducted in a catalytic distillation unit, in a reactor and heat exchanger circulation loop, or in a multi-stage reaction system.

The catalyst employed in the cleavage step can be a homogeneous catalyst or a heterogeneous catalyst.

Suitable homogeneous cumene cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

Suitable heterogeneous catalysts for use in the cleavage of cumene hydroperoxide include solid acid catalysts such as zeolite Beta, disclosed in U.S. Pat. No. 4,490,565; a Constraint Index 1-12 zeolite, such as ZSM-5, disclosed in U.S. Pat. No. 4,490,566; faujasite, disclosed in EP-A-492807; sulfonate-functionalized mesoporous crystalline materials known as M41S materials, e.g. MCM-41, disclosed in U.S. Pat. No. 6,441,251; smectite clays, described in U.S. Pat. No. 4,870,217; ion exchange resins having sulfonic acid functionality or heteropoly acids, such as 12-tungstophosphoric acid, on an inert support, such as silica, alumina, titania and/or zirconia, disclosed in U.S. Pat. No. 4,898,995. Additional solid acid catalysts suitable for use in the cleavage step include those comprising a sulfated transition metal oxide, such as sulfated zirconia, together with an oxide of iron or oxides of iron and manganese, as described in U.S. Pat. No. 6,169,216, as well as those comprising a mixed oxide of cerium and a Group IVB metal, e.g., zirconium, described in U.S. Pat. No. 6,297,406. The entire disclosure of each of the above U.S. patents is incorporated herein by reference.

The cumene hydroperoxide cleavage reaction can also be conducted in the presence of the solid acid catalyst disclosed in U.S. Pat. No. 6,169,215, incorporated herein by reference. Such a catalyst comprises an oxide of a Group IVB metal, such as zirconia or titania, modified with an oxyanion or oxide of a Group VIB metal, such as an oxyanion of chromium, molybdenum or tungsten, treated by calcination of the oxide species at a temperature of at least about 400° C., such as at least about 600° C., for example from about 700° C. to about 750° C. The modification of the Group IVB metal oxide with the oxyanion of the Group VIB metal imparts acid functionality to the material. The catalyst can also contain a metal selected from Groups IB, VIIB, or VIII of the Periodic Table, such as iron, manganese and/or copper.

BPA Production

The products of the cleavage reaction are separated, conveniently by fractionation, into separate phenol and acetone streams. The phenol and at least part of the acetone can then be used for production of the desired BPA.

In general, BPA is produced in accordance with the present invention by (a) reacting acetone with a stoichiometric excess of phenol under acidic conditions, possibly in the presence of a cocatalyst or promoter, e.g. a thiol compound, to form a reaction product stream comprising crude bisphenol-A product, unreacted phenol, possibly unreacted acetone, possibly cocatalyst or promoter if present in the reaction, water of condensation, and other reaction byproducts; (b) distilling in single or multistage the reaction product stream from step (a) to distill off a volatilized unreacted phenol stream, possibly an unreacted acetone stream, possibly a stream containing cocatalyst or promoter if present in step (a) and the water of condensation, while sending the resulting concentrated BPA phenolic feed stream, consisting essentially of phenol in which the bisphenol-A and byproducts have been concentrated, downstream to a BPA-phenol adduct crystallization and purification step, said purification step comprising one or more solid-liquid separation and wash steps; (c) producing BPA-phenol adduct crystals by crystallization of the concentrated BPA phenolic feed stream in each crystallization, solid-liquid separation and wash where cooling for said crystallization utilizes vaporization of an alkane hydrocarbon or mixture of hydrocarbons containing from 4 to 6 carbons, e.g. pentane; (d) separating the BPA-phenol adduct crystals by solid-liquid separation, such as, for example, by centrifugation or filtration, and washing in one or multiple stages the BPA-phenol adduct crystals with a wash phenol stream which may include at least a portion of the volatilized unreacted phenol stream recovered from step (b), or spent wash or mother liquor from subsequent crystallization, solid-liquid separation, and wash steps, to produce final washed BPA-phenol adduct, final spent wash and final mother liquor; (e) cracking a stream comprising at least a portion, for example from about 0.5 to about 20 wt. %, preferably from about 1 to about 10 wt. %, more preferably from about 2 to about 7 wt. %, of said final mother liquor of step (d) in a reactor with basic or acidic cracking catalyst, for example sodium hydroxide or aluminum chloride, under reaction conditions selected to recover a product comprising from about 60 to about 90 wt. % of said stream as phenol having a purity level of from about 95 to about 100 wt. %, and from about 10 to about 40 wt. % of said stream as heavy residue byproduct; and (f) recovering and feeding the phenol product of step (e) to step (a) as phenol reactant and/or step (d) as wash phenol.

The stream comprising the final mother liquor for cracking in step (e) is separated from the product stream, BPA-phenol adduct, of step (d) by any suitable means, such as for example by centrifuge or vacuum filtration.

As detailed herein, BPA is produced by the condensation reaction of excess phenol with acetone in the presence of an acid catalyst. Suitable catalysts for this reaction include inorganic acids, such as sulfuric acid and hydrogen chloride, and cationic exchange resins, optionally together with a cocatalyst or promoter, including a thiol promoter such as an alkyl mercaptan. Non-limiting examples of promoters include methyl mercaptan (MESH), ethyl mercaptan, 2,2-bis(methylthio)propane (BMTP), and mercaptocarboxylic acid, e.g. mercaptopropionic acid. As further non-limiting examples, the condensation reaction may be conducted in the presence of added promoters comprising promoter-bound resins, including resins ionically-bound to quaternary amine groups contained in mercaptoalkylpyridines, or mercaptoalkylamines, the latter most often being 2-mercaptoethylamine derived from hydrolysis of 2,2 dimethylthiozolidine.

More generally, the acid catalyst for step (a) is selected from the group consisting of homogeneous catalysts, heterogeneous catalysts and combinations thereof. The homogeneous acid catalyst is selected from the group consisting of inorganic acids. The heterogeneous acid catalyst is selected from the group consisting of ion exchange resins. The inorganic acid catalyst may be hydrochloric acid, sulfuric acid or a combination thereof. The heterogeneous acid catalyst may include an ion exchange resin, e.g. Lanxess Lewatit K1131S, made from sulfonated polymerized styrene monomer which has been cross linked with from about 1% to about 8% divinylbenzene (resin). The polymer may contain a promoter catalyst that is either ionically or covalently bonded to the polymer resin such as, for example, mercaptoethylamine. Alternatively, an unbound promoter catalyst such as, for example, methyl mercaptan (MESH), ethyl mercaptan or 2,2-bis(methylthiol)propane (BMTP) may also be fed to the reactor containing either a homogeneous or heterogeneous catalyst or combination thereof.

Suitable conditions for the condensation of phenol with acetone to produce BPA include an acetone/phenol molar ratio in the range of from about 1/30 to about 1/3, preferably from about 1/20 to about 1/4, a reaction temperature in the range of from about 40° C. to about 150° C., preferably from about 50° C. to about 100° C., and a weight hourly space velocity (WHSV) of from about 0.2 to about 30 $hr^{-1}$, preferably from about 0.5 to about 20 $hr^{-1}$. The BPA can then be separated from the condensation product as detailed above, e.g. by crystallization.

Reaction conditions of the cracking step, i.e. step (e) above, are selected and controlled to provide high purity phenol for recovery and feeding back to the reaction step (a) as feedstock, and/or to step (d) as high purity wash phenol. Those conditions include a temperature of from about 200° C. to about 350° C., preferably from about 215 to about 260° C., and a pressure of from about 1.33 to 101.3 kPa-a (10 to about 760 mmHg), preferably from about 13.3 to 46.65 kPa-a (100 to about 350 mmHg), and residence time of from about 5 to about 600 minutes, preferably from about 30 to about 200 minutes. The catalyst concentration under these conditions is from about 5 to about 1500 wppm. In this cracking step, there is no intentional addition of inert gases, i.e. nitrogen. The recovered product of this cracking step under these reaction conditions comprises from about 60 to about 90 wt. % of the stream, i.e., portion of mother liquor stream sent to cracking, as phenol, and from about 10 to about 40 wt. % of the stream as heavy residue by-product. Under the above reaction conditions, the phenol portion of the product of this cracking step is high purity, i.e. having a purity level of from about 95 to about 100 wt. %, preferably greater than about 99 wt. %, for example 99.5 wt. %.

It is important to note that cracking step (e) may precede a distillation, follow a distillation or be within a distillation system, e.g. in the distillation bottoms, so long as the cracking conditions are specifically selected as herein detailed to provide the required results. Further, the heavy residue byproduct of step (e) comprises less than about 40 wt. %, preferably from about 0.01 to about 30 wt. %, more preferably from about 1 to about 12 wt. % phenol to allow for ease of processing. The catalyst of step (e) is basic cracking catalyst, for example sodium hydroxide, or acidic cracking catalyst, for example aluminum chloride, zirconium chloride, zirconium sulfate, hydrochloric acid or sulfuric acid.

The following examples are provided for illustrative purposes and do not limit the scope of the invention:

Example 1

A drum size sample of actual mother liquor was taken from a commercial BPA plant that practices the process described herein where BPA-phenol adduct crystals were formed from the vaporization of a C4 to C6 hydrocarbon, and the crystals were washed in a centrifuge in either one or multiple stages with a pure phenol stream to form a pure para-para BPA-phenol adduct solids stream, a mother liquor stream (centrate), and a spent wash stream.

The mother liquor sample from this process had the following approximate composition:

TABLE I

| Component | Weight Percent |
| --- | --- |
| Phenol | 75-77 |
| Bisphenol-A (ortho-para and para-para isomers) | 15-17 |
| Trisphenol-A | 1 |
| Heavies | 5-9 |
| Total | 100 |

A portion of the mother liquor was fed to an experimental cracking apparatus consisting of an Oldershaw column with a condenser overhead and a collection system for the overhead distillate and reflux. The system bottom kettle consisted of a stainless steel kettle with a heating unit. The mother liquor was fed with a stream of caustic (0.25 wt. %) such that the wppm of NaOH in the feed stream was 25 wppm. A bottoms product was withdrawn on a semi-continuous basis while the distillate was constantly withdrawn.

The conditions for the bottom kettle were 215° C. at a pressure of 10.66 kPa-a (80 mmHg). The residence time was about 3.3 hours based on the net bottoms flow.

Table II presents the analytical results of the overhead and bottoms products on a dry basis in weight units for this example with caustic.

TABLE II

| Component | Feed flow (mother liquor portion) | Caustic Flow | Overhead Phenol Product | Bottoms Residue Flow |
| --- | --- | --- | --- | --- |
| Phenol | 299 | 0 | 305 | 5 |
| Bisphenol-A | 69 | 0 | 0 | 38 |
| Trisphenol-A | 4 | 0 | 0 | 9 |
| Heavies | 28 | 0 | 0 | 41 |
| Isopropenylphenol (IPP) | 0 | 0 | 0 | 2 |
| NaOH | | 0.01 | | 0.01 |
| Total | 400 | 0 | 305 | 95 |

The results of this example show a marked increased in the amount of phenol recovered from the top distillate and bottom product (as compared to the feed phenol) such that in a commercial BPA plant, the phenol required for the process would decrease by 0.3%. As can be seen in Table II, only phenol was recovered overhead with no measurable IPP. IPP in the bottoms was also minimal. Recovered phenol was 99.99 wt. % on a dry basis.

Example 2

In this example, the same system was used with a portion of the same mother liquor source as in Example 1. The system was fed with 50 wppm of caustic relative to the mother liquor feed. The operating temperature and pressure of the bottom kettle was 230° C. at 17.3 kPa-a (130 mmHg) with 3.3 hours residence time.

The analytical results of the overhead and bottoms products of this example on a dry basis in weight units are shown in Table III.

TABLE III

| Component | Feed Flow (mother liquor portion) | Caustic Flow | Overhead Phenol Product | Bottoms Residue Flow |
| --- | --- | --- | --- | --- |
| Phenol | 304 | 0 | 328 | 1 |
| Bisphenol-A | 64 | 0 | 0 | 10 |
| Trisphenol-A | 5 | 0 | 0 | 5 |
| Heavies | 27 | 0 | 0 | 54 |
| Isopropenylphenol (IPP) | 0 | 0 | 0 | 2 |
| NaOH | | 0.02 | | 0.02 |
| Total | 400 | 0 | 328 | 72 |

Again, there was a marked increase in the phenol from the system. The phenol taken from the overhead distillate and bottoms was greater than the feed phenol. On a commercial scale basis, the phenol required for the BPA process would decease by 0.7%. As can be seen in the Table III, only phenol was recovered overhead with no measurable IPP. IPP in the bottoms was also minimal. Recovered phenol was 99.99 wt. % on a dry basis.

Example 3

In this example, the same system was used with a portion of the same mother liquor source as in Example 1. The system was fed with 50 wppm of caustic relative to the mother liquor feed. The operating temperature and pressure of the bottom kettle was 230° C. at 10.66 kPa-a (80 mmHg) with 3.3 hours residence time.

The analytical results of the overhead and bottoms products of this example on a dry basis in weight units are shown in Table IV.

TABLE IV

| Component | Feed Flow (mother liquor portion) | Caustic Flow | Overhead Phenol Product | Bottoms Residue Flow |
| --- | --- | --- | --- | --- |
| Phenol | 304 | 0 | 336 | <1 |
| Bisphenol-A | 63 | 0 | 0 | 5 |
| Trisphenol-A | 4 | 0 | 0 | 3 |
| Heavies | 29 | 0 | 0 | 53 |
| Isopropenylphenol (IPP) | 0 | 0 | 0 | 3 |
| NaOH | | 0.02 | | 0.02 |
| Total | 400 | 0 | 336 | 64 |

Again, there is a marked increase in the phenol from the system. The phenol taken from the overhead distillate and bottoms was greater than the feed phenol. On a commercial scale basis, the phenol required for the process would decease by 1%. As can be seen in Table IV, only phenol was recovered overhead with no measurable IPP. IPP in the bottoms was also minimal. Recovered phenol was 99.99 wt. % on a dry basis.

As can be seen from the above specific Examples, essentially no IPP is recovered in the overhead phenol product, and it is a surprising result of this invention that the IPP contained in the bottoms product did not result in the occurrence of polymerization of IPP and the formation of heavies so as to make the system difficult to move hydraulically.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing bisphenol-A comprising the steps of:
   (a) reacting acetone with a stoichiometric excess of phenol under acidic conditions to form a reaction product stream comprising crude bisphenol-A product, unreacted phenol, possibly unreacted acetone, water of condensation, and other reaction byproducts;
   (b) distilling the reaction product stream from step (a) to distill off an unreacted phenol stream, possibly an unreacted acetone stream, and the water of condensation, and sending a concentrated BPA phenolic feed stream consisting essentially of phenol, bisphenol-A and byproducts downstream to BPA-phenol adduct crystallization and purification steps;
   (c) cooling and crystallizing BPA-phenol adduct crystals from the concentrated BPA phenolic feed stream by vaporization of an alkane hydrocarbon or mixture of hydrocarbons containing from 4 to 6 carbons;
   (d) separating BPA-phenol adduct crystals by solid-liquid separation and washing same in one or multiple stages with a phenol wash stream comprising at least a portion of the unreacted phenol stream recovered from step (b), or spent phenol wash or mother liquor streams from subsequent crystallization, solid-liquid separation, and wash steps, to produce final washed BPA-phenol adduct, final spent wash and final mother liquor;
   (e) cracking a stream comprising at least a portion of said final mother liquor of step (d) in a reactor with a basic catalyst under reaction conditions including a temperature from about 200 to about 350° C., a pressure from about 1.33 to 101.3 kPa-a, a residence time from about 5 to about 600 minutes and a catalyst concentration from about 5 to about 1500 wppm, to recover from about 60 to about 90 wt. % of said portion of said final mother liquor cracked stream as phenol having a purity level of from about 95 to about 100 wt. %, and from about 10 to about 40 wt. % of said cracked stream as heavy residue byproduct; and
   (f) recovering and feeding the phenol product of step (e) to step (a) and/or step (d).

2. The process of claim 1 wherein the phenol wash stream of step (d) includes at least a portion of the unreacted phenol stream recovered from step (b).

3. The process of claim 1 wherein the portion of said final mother liquor of step (d) in step (e) is from about 0.5 to about 20 wt. %.

4. The process of claim 1 wherein step (a) is conducted in the presence of an acid catalyst selected from the group consisting of a homogeneous catalyst, a heterogeneous catalyst and combinations thereof.

5. The process of claim 4 wherein step (a) is conducted in the presence of an added promoter selected from the group consisting of methyl mercaptan, ethyl mercaptan, 2,2-bis(methylthio)propane, mercaptocarboxylic acid, and promoter-bound resins.

6. The process of claim 1 wherein the reaction conditions of step (e) include a temperature from about 215 to about 260° C., and a pressure from about 13.3 to 46.7 kPa-a.

7. The process of claim 1 wherein at least a portion of the acetone and phenol of step (a) results from steps comprising:
   (1) contacting benzene and a $C_3$ alkylating agent under alkylation conditions with an alkylation catalyst in a reaction zone to produce an alkylation effluent comprising cumene;
   (2) oxidizing the cumene from step (1) to produce the corresponding hydroperoxide; and
   (3) cleaving the hydroperoxide from step (2) to produce product comprising phenol and acetone;
   and said cracking stream of step (e) comprises from about 0.5 to about 20 wt. % of said final mother liquor of step (d).

8. The process of claim 7 wherein said alkylating agent comprises an aliphatic or aromatic organic compound having one of more available alkylating aliphatic groups of 3 carbon atoms, or mixtures thereof.

9. The process of claim 8 wherein said alkylating agent is selected from the group consisting of propylene, propanol, propionaldehyde, propyl halide and mixtures thereof.

10. The process of claim 7, wherein said alkylation effluent produced in step (1) comprises polyisopropylbenzenes and the process further comprises contacting said polyisopropylbenzenes with benzene in the presence of a transalkylation catalyst to produce cumene.

11. The process of claim 7, wherein the cleaving step (3) is conducted in the presence of a catalyst comprising at least one of sulfuric acid, perchloric acid, phosphoric acid, hydrochloric acid, p-toluenesulfonic acid, ferric chloride, boron trifluoride, sulfur dioxide and sulfur trioxide.

12. The process claim 7, wherein the cleaving step (3) is conducted at a temperature from about 20° C. to about 150° C., a pressure from about 0 to about 7000 kPa and a liquid hourly space velocity (LHSV) based on the hydroperoxide from about 0.1 to about 100 $hr^{-1}$.

13. The process of claim 7, wherein step (a) is conducted in the presence of an added promoter selected from the group consisting of methyl mercaptan, ethyl mercaptan, 2,2-bis(methylthio)propane, mercaptocarboxylic acid, and promoter-bound resins.

14. The process of claim 7, wherein the reaction conditions of step (e) include a temperature from about 215 to about 260° C., and a pressure from about 13.3 to 46.7 kPa-a.

* * * * *